United States Patent [19]
Leon Rolden et al.

[11] Patent Number: 5,843,185
[45] Date of Patent: Dec. 1, 1998

[54] KERATOPROSTHESIS AND METHOD OF CORNEAL REPLACEMENT

[76] Inventors: Carlos R. Leon Rolden, 1a Calle 30-80 Zona 7 Utatlan I, Guatemala City, Guatemala; Jose I. Barraquer Granados, 100 Ave. No. 18A-51, Bogota, Colo.

[21] Appl. No.: 740,005

[22] Filed: Oct. 23, 1996

[51] Int. Cl.⁶ .................................................. A61F 2/14
[52] U.S. Cl. ................................................. 623/5; 623/4
[58] Field of Search ........................................... 623/4–6

[56] References Cited

U.S. PATENT DOCUMENTS

| | | | |
|---|---|---|---|
| 3,929,971 | 12/1975 | Roy | 623/16 |
| 4,264,493 | 4/1981 | Battista | 623/4 |
| 4,314,380 | 2/1982 | Miyata et al. | 623/16 |
| 4,466,705 | 8/1984 | Michelson | 623/4 |
| 4,470,159 | 9/1984 | Peyman . | |
| 4,586,929 | 5/1986 | Binder . | |
| 4,612,012 | 9/1986 | White . | |
| 4,647,282 | 3/1987 | Fedorov et al. . | |
| 4,693,715 | 9/1987 | Abel, Jr. . | |
| 4,772,283 | 9/1988 | White . | |
| 4,842,599 | 6/1989 | Bronstein . | |
| 4,865,601 | 9/1989 | Caldwell et al. . | |
| 4,923,466 | 5/1990 | Pintucci . | |
| 4,976,731 | 12/1990 | Perry . | |
| 5,030,230 | 7/1991 | White . | |
| 5,067,961 | 11/1991 | Kelman et al. . | |
| 5,108,428 | 4/1992 | Capecchi et al. . | |
| 5,171,318 | 12/1992 | Gibson et al. . | |
| 5,192,293 | 3/1993 | Cartwright et al. | 606/172 |
| 5,192,316 | 3/1993 | Ting . | |
| 5,300,116 | 4/1994 | Chirila et al. . | |
| 5,326,346 | 7/1994 | Cortes | 623/4 |
| 5,344,452 | 9/1994 | Lemperle . | |
| 5,354,332 | 10/1994 | Lacombe . | |
| 5,383,935 | 1/1995 | Shirkhanzadeh | 623/16 |
| 5,466,258 | 11/1995 | Rubin | 623/4 |
| 5,466,259 | 11/1995 | Durette . | |
| 5,489,300 | 2/1996 | Capecchi et al. . | |
| 5,489,301 | 2/1996 | Barber . | |

Primary Examiner—Michael J. Milano
Assistant Examiner—Tram Anh T. Nguyen
Attorney, Agent, or Firm—Malloy & Malloy, P.A.

[57] ABSTRACT

An improved keratoprosthesis, to be utilized to enhance a patient's vision, which includes an optical support segment structured to be disposed on an eyeball of the patient and containing an optical aperture, structured to be disposed in aligned, overlying relation to a corneal region of the eyeball of the patient, defined therein. Further, the optical support segment includes a disc like configuration and is constructed of hydroxyapatite which is structured and disposed to promote cell growth, increased vascularization and/or bone formation therein so as to substantially increase the optical support segment's long term assimilation with the eyeball of the patient, as well as its ability to combat infection and heal quickly. Disposed in the optical aperture of the optical support segment and effectively suspended in a vision enhancing position is an optical cylinder. The optical cylinder is preferably removable and provides for the transmittal of light into the eyeball.

22 Claims, 4 Drawing Sheets

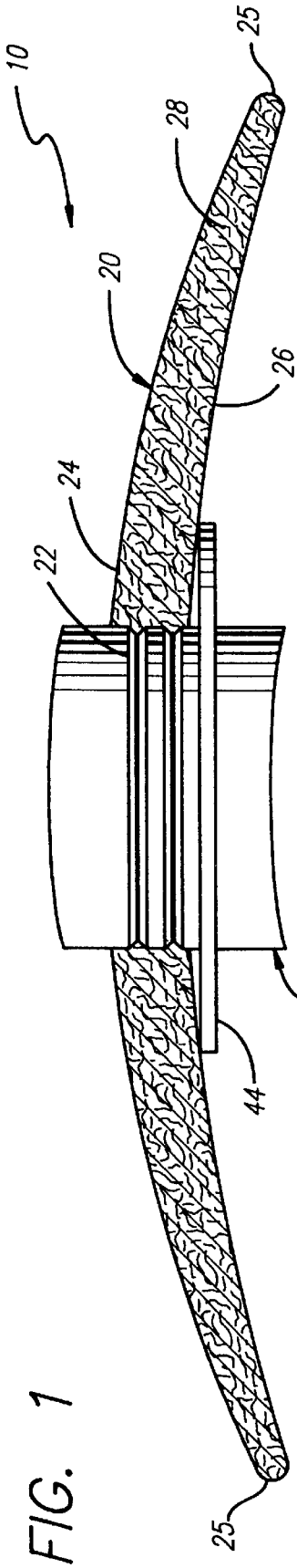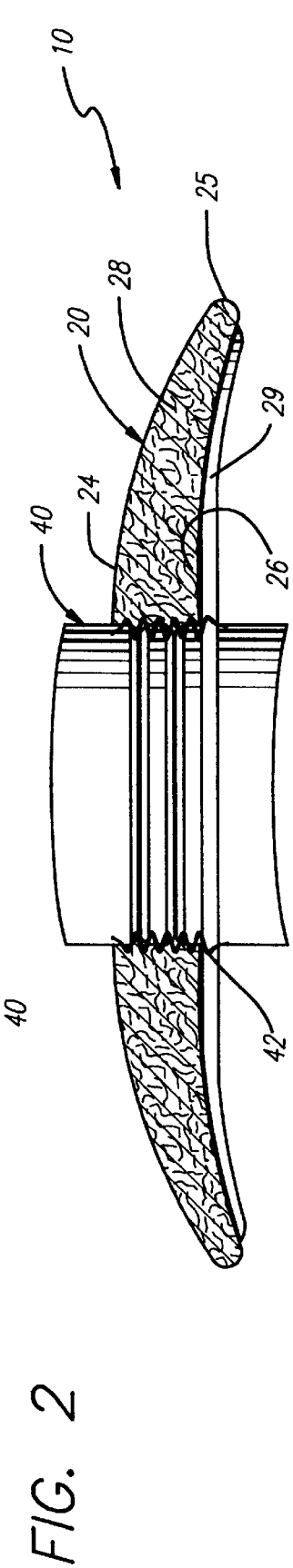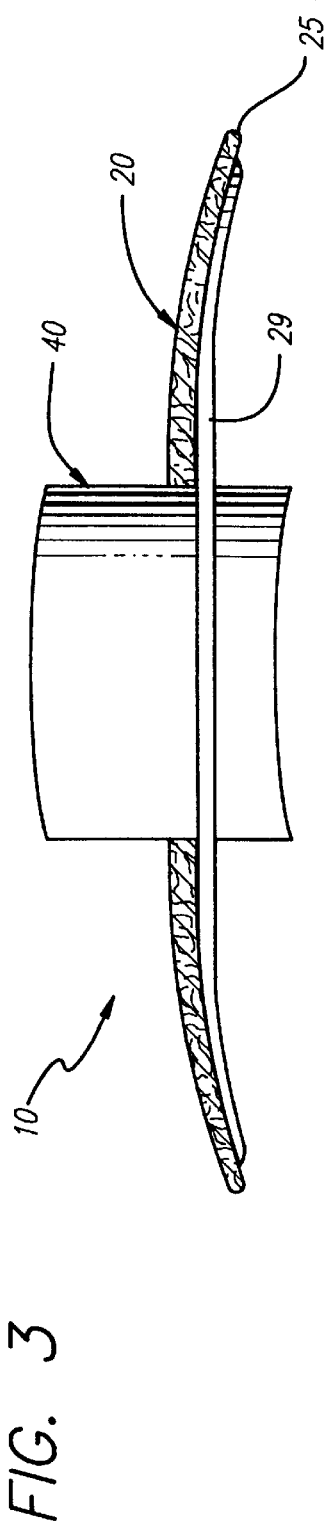

KERATOPROSTHESIS AND METHOD OF CORNEAL REPLACEMENT

BACKGROUND OF THE INVENTION

1. Field of the Invention

The present invention relates to an improved keratoprosthesis and method of corneal replacement which provides for the effective and complete assimilation of the keratoprosthesis with the living eyeball in a manner which will not be readily rejected by the living organism, can be effectively configured to an effective and appropriate shape, and achieves enhanced recovery for long term use with a support that is bio-compatible and bio-integrable so as to promote colonization by fibrovascular tissue and/or bone formation.

2. Description of the Related Art

The use of a keratoprosthesis for the replacement of all or part of the cornea of a living organism is a continuously growing and evolving technology in the field of art relating to vision restorative ophtholonological surgery. While the benefits of positioning an optical cylinder or lens to let images pass to the retina of a patient's eyeball are understood, substantial drawbacks continue to exist in the manner in which that optical cylinder or lens is effectively positioned.

In particular, the optical cylinder or lens must generally be supported by a support (haptic) region that comprises a primary portion of the keratoprosthesis. Moreover, that support region of the keratoprosthesis must be secured directly to the eyeball, thereby providing for the maintenance of effective aligned positioning of the optical cylinder during a full range of movement of the eyeball. In order to accommodate for the constantly moving support surface, a variety of techniques are employed in an attempt to effectively secure and maintain the keratoprosthesis in position on the eyeball. For example, existing techniques often incorporate adhesives or suturing procedures so as to effectively provide for securing of the support region of the keratoprosthesis. Unfortunately, however, existing procedures have not proven adequate for long term utilization, and the development of improved, advanced, and more effective support structures for the optical cylinder is a primary area of research and development in this field. Specifically, many different types of keratoprosthesis support structures, which usually only vary with regard to the configuration and construction of the support structure, have been developed in an attempt to improve connection with the eyeball utilizing minor variations. Even so, the need for a more effectively assimilating keratoprosthesis is present.

A significant reason for the failure of currently implemented support structures and keratoprosthesis configurations relates to the body's natural tendency to refuse complete integration of foreign matter and the active environment of the eyeball. In particular, the adhesives and stitching that must be utilized with existing configurations generally tend to wear over time, especially in the environment of a living, moving eyeball, dislodging or misalignment of the keratoprosthesis can result with existing designs. Further, because the support itself is a foreign object that is in contact with the eyeball, true assimilation generally does not take place with the living eyeball. Specifically, the support structures of known keratoprosthesis assemblies are generally formed of polymers or other synthetic materials which may be generally bio-compatible, but are not bio-integrable or bio-ionizable. Accordingly, the body tends to not interact effectively with the keratoprosthesis over time which can lead to complications, such as serious infection or poor healing after trauma.

As a result, there is still a substantial need in the art for an improved keratoprosthesis which is effective for restoring vision to a patient and can be effectively implemented with a living eyeball, but which is also substantially bio-compatible, bio-colonizable, bio-integrable and not bio-absorbable and can assimilate with the patient's eyeball in an effective manner, thereby reducing the risk of rejection by the body and significantly extending the useful life of the keratoprosthesis beyond that of currently implemented configurations. Additionally, such an improved keratoprosthesis should function to promote complete vascularization and bone growth in order to promote adoption of the keratoprosthesis as part of the cellular structure of the eyeball.

It is also noted that the present invention incorporates a unique adaptation of hydroxyapatite in a previously uncontemplated adaptation. Specifically, hydroxyapatite has been experimented with in other applications, such as in bone replacement and in dentistry for post extraction procedures in order to study its acceptance by the body. Moreover, some have utilized the hydroxyapatite to repair orbital fractures and in the formation of orbital implants to replace the entire globe after enucleation, evisceration or as a secondary implant. Given the substantially specialized environment relating to vision restoration, and the significantly different circumstances associated with providing an implant on a living, functioning eyeball, the use of such a material has, prior the present invention, never been suggested for use and/or tested in such a unique application. In particular, vision restoration, such as that accomplished utilizing a keratoprosthesis, must interact with the living eyeball and preserve whatever functioning is present by the eyeball for interaction with the prosthesis. Unlike a bone or tooth reparation, or even the implementation of an orbital implant, the specialized functions of the organism need not be preserved, but rather a structure to merely "fill" an area is needed.

As such, there is still a need in the art for an improved keratoprosthesis and method of corneal replacement that is structured to actually interact with the living eyeball so as to restore normal vision in a manner which can be accepted by the human organism. The device of the present invention provides for such a unique adaptation and implementation, as well as method which significantly promotes bone growth and/or colonization/ingrowth by fibrovascular tissue, and expedites recovery time for a long term restorative effect.

SUMMARY OF THE INVENTION

The present invention relates to an improved keratoprosthesis to be utilized to enhance a patient's vision, and be positioned directly on and interact with a living eyeball of the patient. Specifically, the keratoprosthesis includes an optical support segment that is structured to be disposed on the eyeball of the patient. The optical support segment, which preferably has a disc-like configuration, includes an optical aperture defined therein and structured to be positioned in an aligned, overlying relation to a pupil region of the eyeball of the patient.

Moreover, the optical aperture is structured to receive an optical cylinder therein. It is the optical cylinder that provides a light transmitting medium through which light is permitted to pass into the eyeball. As such, the optical cylinder is maintained in proper light transmitting position and alignment by the optical support segment, and functions to enhance the vision of the patient.

In order to increase the effective securing of the optical support segment on the eyeball of the patient, the optical support segment is constructed at least partially of hydroxyapatite. The hydroxyapatite, which is preferably porous, is structured and disposed to promote cell growth, fibrovascular tissue ingrowth and/or bone formation therein. As a result, the optical support segments long term assimilation with the eyeball of the patient is substantially increased and the optical cylinder remains effectively positioned for extended, effective use as bone formation occurs within the pores of the optical support segment.

It is an object of the present invention to provide an improved keratoprosthesis and method of corneal replacement which is substantially bio-compatible, bio-colonizable, bio-integrable and not bio-absorbable in order to provide for effective long term utilization.

A further object of the present invention is to provide an improved keratoprosthesis which is structured so as to promote cell growth and bone formation therein, thereby effectuating substantially complete assimilation with the living eyeball of the patient.

Another object of the present invention is to provide an improved keratoprosthesis which is structured so as to promote cell growth and fibrovascular tissue ingrowth therein, thereby effectuating substantially complete assimilation with the living eyeball of the patient.

Yet another object of the present invention is to provide an improved keratoprosthesis which is formed of a material which enables precise, well-defined formation while still substantially promoting vascularization and assimilation with the patient's eyeball.

An additional object of the present invention is to provide a method of corneal replacement which is structured to provide for long term assimilation and substantially rapid healing.

An additional object of the present invention is to provide an improved keratoprosthesis which interacts with and does not detract from the functioning of the eyeball to its capabilities.

BRIEF DESCRIPTION OF THE DRAWINGS

For a fuller understanding of the nature of the present invention, reference should be had to the following detailed description taken in connection with the accompanying drawings in which:

FIG. 1 is cross-sectional view of a preferred keratoprosthesis of the present invention;

FIG. 2 is an alternative embodiment of the keratoprosthesis of the present invention;

FIG. 3 is another alternative embodiment of the keratoprosthesis of the present invention;

Like reference numerals refer to like parts throughout the several views of the drawings.

DETAILED DESCRIPTION OF THE PREFERRED EMBODIMENT

Shown throughout the Figures, the present invention is directed towards an improved keratoprosthesis, generally indicated as 10. The keratoprosthesis is structured to be implemented in combination with a living eyeball in order to enhance a patient's vision, and in many instances restore completely lost vision to the patient. Furthermore, the improved keratoprosthesis of the present invention is structured to be implanted directly on the eyeball either atop the cornea or in an interlamellar position beneath the exterior surfaces of the eyeball in order to provide for the passage of light into the patient's eyeball.

Figure 4A:
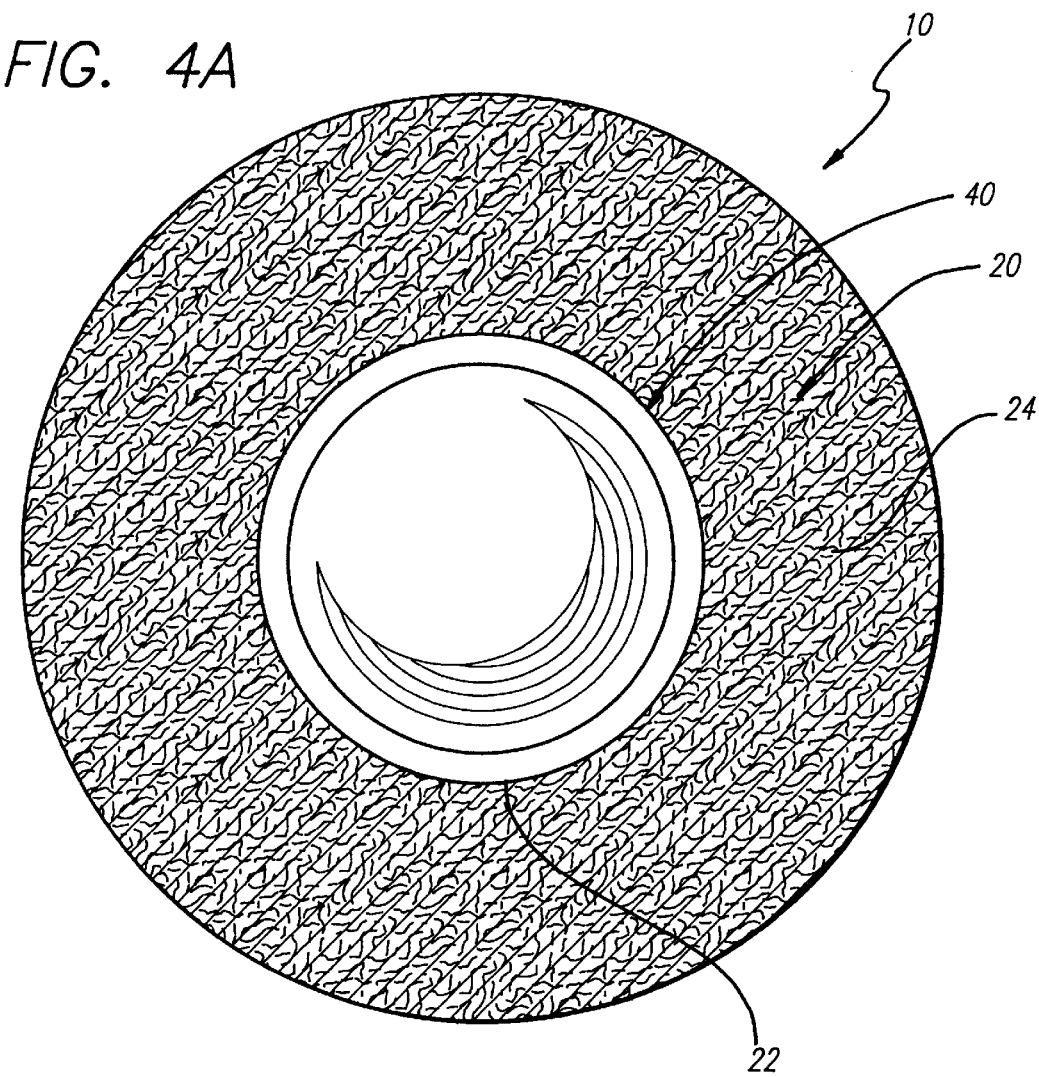
FIG. 4A is a top plan view of the keratoprosthesis of the present invention.
Figure 5A:
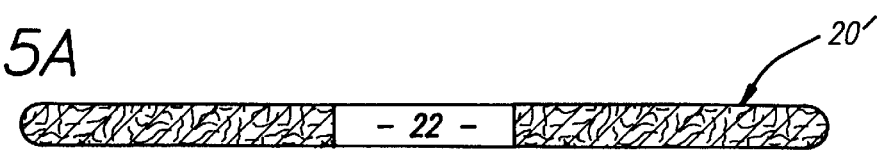
FIGS. 5A, 5B, and 5C are series of schematic illustrations of alternative cross-sectional profiles of the optical support segment of the present invention.
Figure 5B:
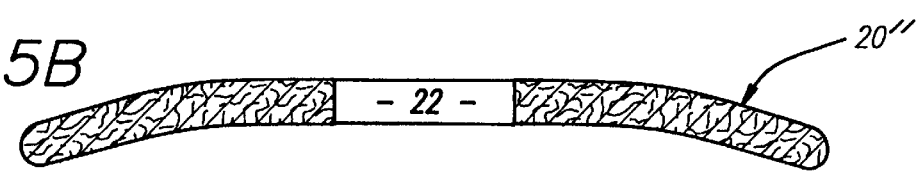
Figure 5C:
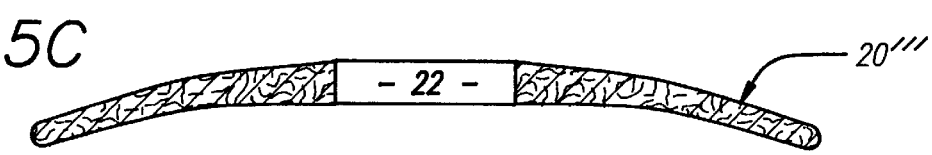

The improved keratoprosthesis 10 of the present invention includes an optical support segment 20. The optical support segment 20, which includes a preferably smooth, uniform upper surface 24 and lower surface 26, is structured to be disposed directly on the eyeball of the patient in aligned, overlying relation to the cornea. Moreover, the optical support segment 20 preferably includes a generally disc-like configuration to correspond the patient's eyeball and to more effectively engage the patient's eyeball. In the preferred embodiment, the optical support segment includes a diameter of approximately between 5 millimeters and 15 millimeters. Moreover, as illustrated in FIGS. 5A, 5B and 5C, a series of cross-sectional profiles 20', 20", and 20''', may also be provided to accommodate for effective abutting engagement of the optical support segment 20 with the patient's eyeball. Of course, a variety of additional alternative cross-sectional configurations could also be implemented so long as a surface area of the optical support segment 20 is sufficient to permit effective engagement with the eyeball to be maintained. Furthermore, so as to provide a more uniform transition between the optical support segment 20 and the eyeball, a perimeter 25 of the optical support segment 20 includes a narrowing taper. As such, as the optical support segment 20 will be generally centered on the eyeball, it is preferred that a generally rounded configuration terminating in the narrowed taper be utilized to preserve the round, optimal configuration of the overall eyeball as it moves through the orbital socket. Further, the optical support segment 20 will also preferably include a concave lower surface 26 which minimizes the exterior profile of the keratoprosthesis 10 beyond the eyeball and provides for effective mating engagement with the surface of the eyeball.

Defined in the optical support segment 20, is an optical aperture 22. Specifically, the optical aperture 22 is an opening disposed in aligned, overlying relation to the cornea of the eyeball of the patient, preferably concentrically over the pupil region of the eyeball, and extending completely through the optical support segment 20. In the preferred embodiment, the optical aperture 22 includes a generally round configuration, with an optimal diameter of about between 1 millimeter and 10 millimeters depending upon the needs of the patient for light transmittal.

The optical aperture 22 of the optical support segment 20 is structured to receive an optical cylinder 40 therein. The optical cylinder 40 is preferably structured to act at a lens for the transmittal of light into the eyeball, thereby achieving the desired vision enhancement. It is therefore seen that the optical support segment 20 acts as a support to effectively suspend and position the optical cylinder 40 in a desired, operative orientation. Moreover, it is understood that a variety of differing configurations of optical cylinders 40 may be effectively incorporated as part of the improved keratoprosthesis 10 of the present invention, the particular configuration and/or lens structure of the optical cylinder 40 depending upon the needs of the user and/or the vision correction required by the patient.

Figure 8:
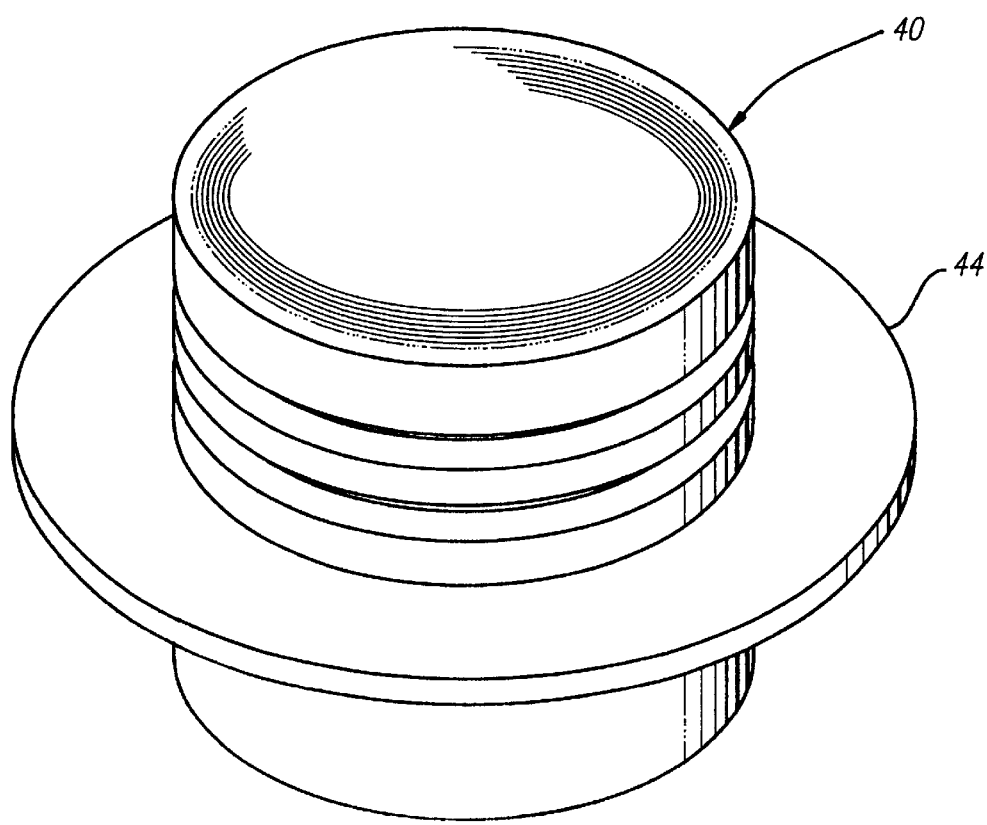
FIG. 8 is an isolated perspective view of the optical cylinder of the present invention.

The optical cylinder 40 is preferably substantially securely coupled with the optical support segment 20 in order to achieve that secure positioning, and may in fact be permanently secured thereto. In this regard, in a first embodiment of the keratoprosthesis, as illustrated in FIG. 1 and 8, the optical cylinder 40 includes a flange element 44. The flange element 44, which preferably extends completely (360°) about the optical cylinder 40, is structured to be secured with the optical support segment 20, such as by a strong adhesive. Of course, as this coupled engagement therebetween is to be achieved before the keratoprosthesis 10 is implanted, a variety of effective alternative methods could be implemented in order to achieve effective secure coupling therebetween. For example, the optical cylinder could be directly adhered to the optical support segment 20, utilizing a cement that does not affect the vitality of the hydroxyapatite, or the flange element 44 could be implanted within the optical support segment 20. Additionally, as in the embodiment of FIG. 2, the optical cylinder 40 may be structured for removable engagement with the optical support segment 20, such as utilizing a threaded engagement 42. Such removable engagement would be effective to permit replaceability of only the optical cylinder 40 if differing vision correction is required at a future date. Due to the substantial integration of the optical support segment 20 of the keratoprosthesis 10 of the present invention with the eyeball, as is to be described, a removable optical cylinder 40 can be especially effective if varying vision correction is a possibility.

In particular, in order to substantially increase the optical support segment's 20, long term assimilation with the eyeball of the patient, the optical support segment 20 of the improved keratoprosthesis 10 of the present invention is constructed at least partially of hydroxyapatite 28. The hydroxyapatite 28, which is usually a derivative of calcium carbonate that has undergone a hydrothermal exchange reaction, is utilized to promote cell growth and bone formation therein, and thereby substantially increase that long term assimilation. In the preferred embodiment of the present invention, the hydroxyapatite is naturally produced, porous hydroxyapatite 28 derived from calcite or aragonite. Of course, a variety of different types of hydroxyapatite, both porous and granular may be utilized, such as synthetic hydroxyapatite, low density hydroxyapatite, dense hydroxyapatite, dense hydroxyapatite matrix, low density hydroxyapatite sheets, natural mammalian bone hydroxyapatite, or any alternative hydroxyapatite source whether natural or synthetic which can be effectively configured. Specifically, the preferred porous hydroxyapatite 28 includes a plurality of pores formed therein and interconnecting throughout the hydroxyapatite 28. These pores permit extensive vascularization and cell formation so that after an extended period of use, actual fibrovascular tissue ingrowth and/or bone formation occurs and the optical support segment 20, with the hydroxyapatite construction, is more effectively assimilated with the living eyeball and helps to prevent infection. In fact, unlike synthetic or alternative configurations, rejection by the body is significantly reduced and the resultant cell growth and assimilation can be quite rapid and effective due to the bio-compatible, bio-colonizable, bio-integrable and non bio-absorbable nature of the hydroxyapatite 28. Accordingly, an embodiment wherein the optical cylinder 40 may be removed is particularly effective as the support for the optical cylinder 40 can remain effectively secured and in place over time and a new assimilation process need not be undertaken if adjustment of the optical cylinder 40 is required.

As indicated, in the preferred embodiment of the present invention porous hydroxyapatite is utilized to form the optical support segment. Additionally, however, it is preferred that the plurality of pores defined in the porous hydroxyapatite have diameters of between approximately 60 microns and 240 microns with a maximum range of about between 10 and 400 microns. In this regard, it is seen that hydroxyapatite which is aragonite based or calcite based is preferred as they provide pores in the ranges of 60 to 260 microns or 100 to 120 microns, which are sufficient to effectively promote the cell growth in a highly effective manner. Moreover, unlike hydroxyapatite which may be utilized in bone replacement, orbital fractures or orbital implants, and generally include pores of much larger diameters (i.e. 400–800 microns), it is preferred that the smaller diameter pores be implemented to allow the precision formation of the diminutive dimensions of the preferred optical support segment 20 utilized in the keratoprosthesis 10. Specifically, it is seen that hydroxyapatite with larger pores will more easily break or disintegrate when formed into the substantially thin preferred configurations of the optical support segment 20. In the preferred embodiment the optical support segment 20 will have a thickness of approximately 1 to 1.5 millimeters at its thickest region, although varying dimensions ranging from about 10 microns to 4 mm may be implemented as deemed necessary.

Figure 4B:
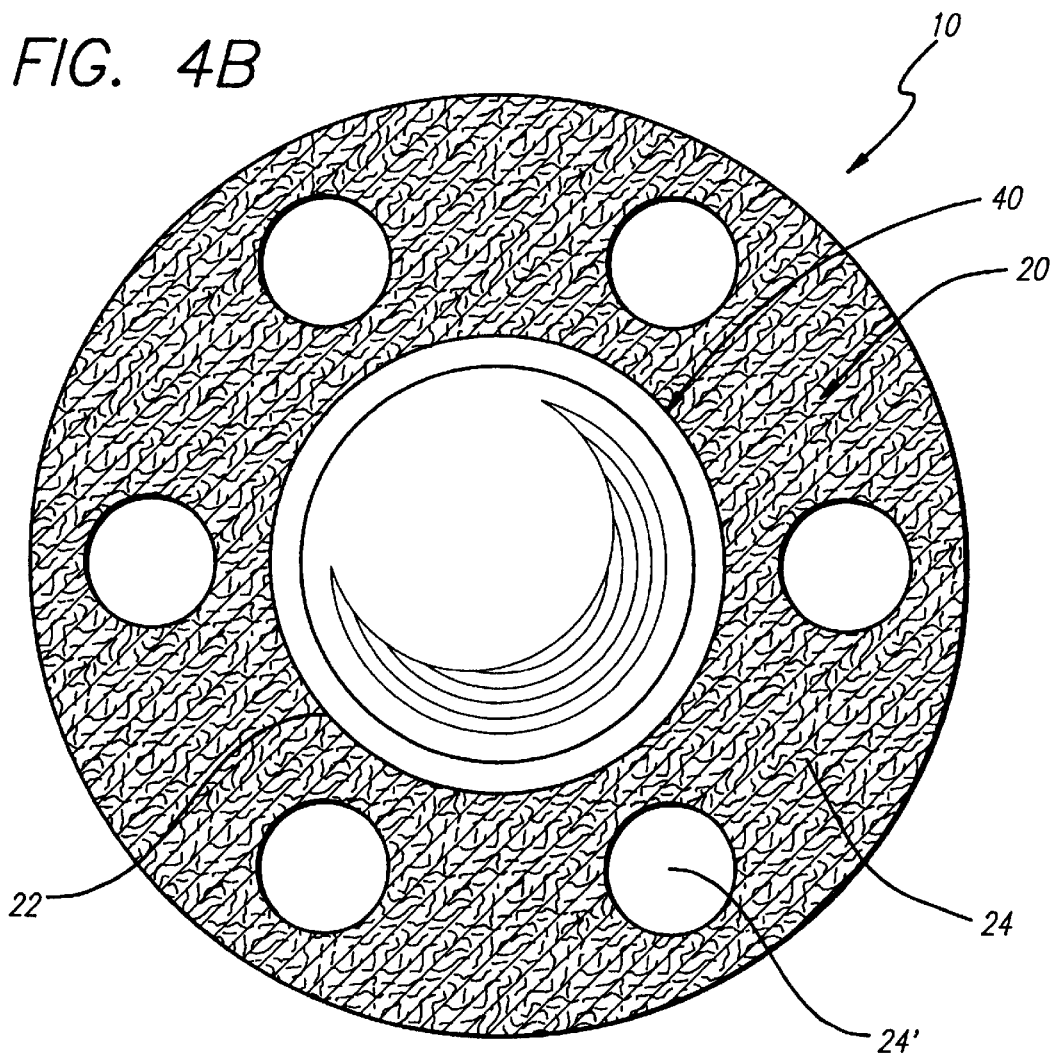
FIG. 4B is a top plan view of another embodiment of the keratoprosthesis of the present invention.

Moreover, in either the porous hydroxyapatite embodiment or the granular hydroxyapatite embodiment the optical support segment 20 may further include a synthetic reinforcement layer 29, such as in FIGS. 2 and 3 which provides the optical support segment 20 with added strength and could minimize the quantity of hydroxyapatite 28 which must be obtained. In this regard, the synthetic reinforcement layer 29 defines a polymer base that preferably extends completely along the lower surface 26 of the hydroxyapatite portion 28 of the optical support segment 20, as in FIG. 2, or may extend just partially therealong. Moreover, a series of holes 24' as in FIG. 4B may provided to reduce the overall weight of the support segment 20 and to reduce the amount of hydroxyapatite which must be utilized. Further, if desired, only small amounts of the hydroxyapatite region 28, as in FIG. 3, may be implemented with a larger synthetic reinforcement layer 29 to provide a substantial portion of the optical support segment 20. Still, however, it is preferred that the hydroxyapatite 28 provide a substantial, if not complete, formation of the optical support segment 20 as it will provide the area at which cell growth and fibrovascular tissue ingrowth will actually be achieved.

In addition to the benefits to utilizing the hydroxyapatite 28 for the formation of the optical support segment 20, in an embodiment of the present invention a protein layer may also be disposed on the optical support segment 20. Specifically, the protein layer preferably includes enzymatic bone morphogenic protein which is absorbed and stored by the hydroxyapatite 28 for subsequent controlled, timed release. As a result, the bone morphogenic protein can effectively initiate cell growth and bone formation throughout the hydroxyapatite, which preferably is completely soaked in the protein layer, over an extended period of time, thereby promoting healing and vascularization for substantial assimilation between the optical support segment 20 of the keratoprosthesis 10 and the living eyeball. Alternatively, a growth factor substance can be added in a similar fashion for absorption by the hydroxyapatite, the growth factor substance being of the type which promotes fibrovascular tissue growth and/or cell growth.

The improved keratoprosthesis 10 of the present invention is further incorporated as part of a method of corneal replacement. Specifically, the method of corneal replacement, which may be implemented for complete or partial corneal replacement, begins with an initial step of forming an optical support segment 20 at least partially from a quantity of hydroxyapatite 28. Furthermore, as indicated, it is preferred that the optical support segment 20 be formed entirely of porous hydroxyapatite 28. Next, in a preferred methodology, a quantity of bone morphogenic protein is applied to the optical support segment 20 by soaking the optical support segment 20 in the quantity of bone morphogenic protein for an extended period of time. As a result, the bone morphogenic protein is completely absorbed throughout the hydroxyapatite 28 configuration of the optical support segment 20 for subsequent timed release to promote cell growth.

Either before or after the subsequent steps, the optical cylinder 40 is secured to the optical support segment 20. From this it is seen that the optical cylinder 40 may be implemented either upon initial formation of the optical support segment or at any time throughout the procedure as deemed appropriate by the physician performing the surgical procedure, and in fact, if deemed to be effective may be completely omitted should the optical aperture defined in the optical support segment 20 be sufficient for vision enhancement.

Next, the patient's eyeball is shaped such that it is capable of receiving the optical support segment 20 thereon, and the optical support segment 20 is positioned on the patient's eyeball. Finally, the optical support segment 20 is secured in an aligned orientation on the patient's eyeball such that the optical cylinder 40 may effectively operate to enhance the patient's vision.

Figure 6A:
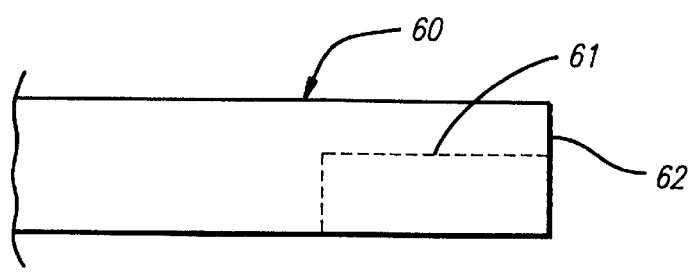
FIGS. 6A and 6B are a series of perspective illustrations of optical musculature illustrating the preferred preparation of the patient's eyeball to receive the optical support segments.
Figure 6B:
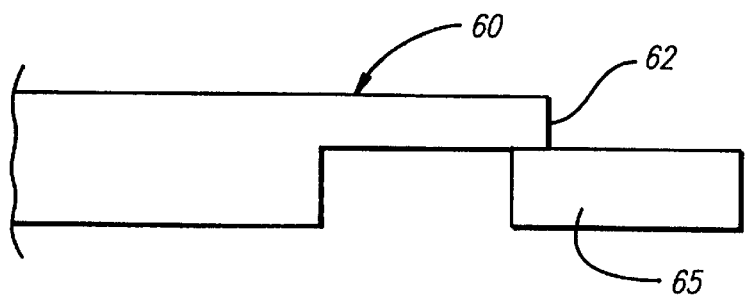
Figure 7:
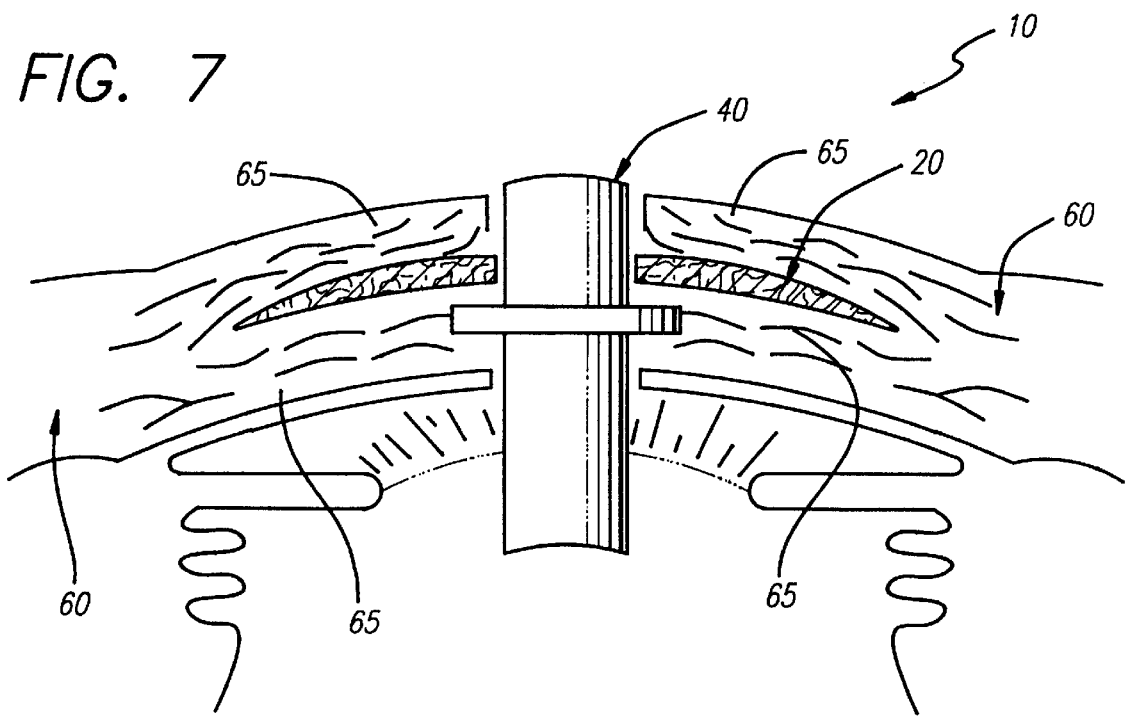
FIG. 7 is a cross-section view of the forward regions of the eyeball with the keratoprosthesis in place.

Looking more specifically to the step of shaping the patient's eyeball such that it is capable of receiving the optical support segment 20, a series of additional steps may be included. In particular, turning to FIGS. 6A and 6B, an additional step of cutting at least one, but preferably a plurality of flaps 60 of optical musculature may be included. Specifically, optical musculature is generally present within the ocular cavity and secures the eyeball in place providing for necessary movement of the eyeball. In the method of the present invention, a flap 60 of that optical musculature is cut and extended into engagement with the optical support segment 20. Furthermore, as the available flaps 60 of optical musculature are generally not sufficiently elongate to extend around into engagement with the optical support segment 20, it is preferred that the additional step of partially severing the flap 60 of optical musculature so as to define an extension segment 65 be performed. In particular, looking to FIG. 6A, an incision along dotted line 61 is formed such that the extension segment 65, which is still secure to the flap 60, is formed. That extension segment 65 is overlapped into an extended orientation beyond a distal end 62 of the flap 60, the natural point of attachment of the musculature to the sclera. Moreover, if desired this step may be performed again with a further extension segment being cut and overlapped from the initially formed extension segment 65. It should be noted that each flap 60 will generally include two major arteries to provide a continuous flow such that the cutting and inversion of an extension segment 65 including one of the major arteries is preferred and also functions to invert the blood flow such that the blood in fact must flow to the optical support segment 20. Specifically, once cut and overlapped the extension segment 65 that is formed is extended into engaging relation with a radially interior region of the optical support segment 20. In this regard, although the extension segments 65 may be positioned in overlying relation atop the upper surface 24 of the optical support segment 20, it is preferred that the extension segment 65 be disposed to abut the lower surface 26 of the optical support segment 20, and/or both the upper and lower surfaces 24 and 26, as illustrated in FIG. 7, and extend towards the optical aperture 22 defined in the optical support segment 20. In fact, it may be preferable to extend the extension segment 65 axially into the optical aperture 22 of the optical support segment 20, such as between the optical cylinder 40 and the optical support segment 20. With this effective positioning of the optical musculature by way of the extension segment 65, it is seen that vascularization and cell growth is initiated at both the radially interior regions and radially exterior regions of the optical support segment 20 due both to a reverse in the direction of blood flow within the musculature because of the overlapping and the presence of a blood flow at the radially interior regions. As a result, recovery time is substantially expedited as the cell growth creeps in multiple directions. In fact, such a procedure provides a higher flow of blood and dramatically accelerates integration of the optical support segment 20 with the eyeball, and although not necessary, is preferred.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. To be utilized to enhance a patient's vision, an improved keratoprosthesis comprising:

an optical support segment, said optical support segment being structured to be disposed in assimilating engagement with an ocular musculature of on a living eyeball of the patient, an optical aperture defined in said optical support segment and structured to be disposed in aligned, relation to a cornea of the eyeball of the patient, an optical cylinder disposed in said optical aperture, and said optical support segment is constructed at least partially of hydroxyapatite structured and disposed to promote cell growth and vascularization therein so as to substantially increase said optical support segment's long term assimilation with the eyeball of the patient.

2. An improved keratoprosthesis as recited in claim 1 further including a protein layer disposed on said optical support segment and structured to promote bone growth and assimilation.

3. An improved keratoprosthesis as recited in claim 2 wherein said protein layer includes bone morphogenic protein.

4. An improved keratoprosthesis as recited in claim 3 wherein said bone morphogenic protein is absorbed and stored by said hydroxyapatite for subsequent controlled timed release thereby to initiate cell growth and bone formation.

5. An improved keratoprosthesis as recited in claim 1 further including a growth factor substance disposed on said optical support segment and structured to promote assimilation.

6. An improved keratoprosthesis as recited in claim 1 wherein said hydroxyapatite includes porous hydroxyapatite.

7. An improved keratoprosthesis as recited in claim 6 wherein said porous hydroxyapatite includes a plurality of pores defined therein and having diameters of between approximately 10 microns and 400 microns.

8. An improved keratoprosthesis as recited in claim 1 wherein said hydroxyapatite includes granular hydroxyapatite.

9. An improved keratoprosthesis as recited in claim 1 wherein said optical support segment further includes a synthetic reinforcement layer structured to provide said optical support segment with added strength.

10. An improved keratoprosthesis as recited in claim 1 wherein said hydroxyapatite is aragonite based.

11. An improved keratoprosthesis as recited in claim 1 wherein said hydroxyapatite is calcite based.

12. An improved keratoprosthesis as recited in claim 1 wherein said hydroxyapatite includes a dense hydroxyapatite matrix.

13. An improved keratoprosthesis as recited in claim 1 wherein said hydroxyapatite includes at least one low density hydroxyapatite sheet.

14. An improved keratoprosthesis as recited in claim 1 wherein said hydroxyapatite includes natural mammalian bone hydroxyapatite.

15. An improved keratoprosthesis as recited in claim 1 wherein said optical cylinder includes a flange element structured to be secured with said optical support segment.

16. An improved keratoprosthesis as recited in claim 1 wherein said optical support segment includes a generally disk-like configuration.

17. An improved keratoprosthesis as recited in claim 16 wherein said optical support segment includes a diameter of about between 5 mm and 15 mm.

18. An improved keratoprosthesis as recited in claim 1 wherein said optical aperture includes a diameter of about between 1 mm and 10 mm.

19. An improved keratoprosthesis as recited in claim 1 wherein a perimeter of said optical support segment includes a narrowing taper so as to provide a more uniform transition between said optical support segment and the eyeball.

20. An improved keratoprosthesis as recited in claim 1 wherein said optical support segment includes a concave lower surface.

21. An improved keratoprosthesis as recited in claim 1 wherein a lower surface of said optical support segment is structured to correspond a surface configuration of the eyeball.

22. To be utilized to enhance a patient's vision, an improved keratoprosthesis comprising:

an optical support segment, said optical support segment being structured to be disposed in assimilating engagement with an ocular musculature of the eyeball of the patient, an optical aperture defined in said optical support segment and structured to be disposed in aligned, relation to a cornea of the eyeball of the patient, an optical cylinder disposed in said optical aperture, said optical support segment is constructed at least partially of hydroxyapatite structured and disposed to promote cell growth and vascularization therein so as to substantially increase said optical support segment's long term assimilation with the eyeball of the patient, and said optical support segment further including a synthetic reinforcement layer integrally disposed therewith and structured to provide said optical support segment with added strength.

* * * * *